United States Patent [19]
Fabricant

[11] Patent Number: 5,665,060
[45] Date of Patent: Sep. 9, 1997

[54] BUNION TREATMENT APPARATUS AND METHOD

[75] Inventor: B. Robert Fabricant, Boca Raton, Fla.

[73] Assignee: Dr. Fabricant's Foot Health Products, Inc., Hauppauge, N.Y.

[21] Appl. No.: 573,022

[22] Filed: Dec. 15, 1995

[51] Int. Cl.[6] ............................................. A61F 5/00
[52] U.S. Cl. ............................ 602/30; 128/893; 128/394
[58] Field of Search ................... 602/30, 31; 128/889–894

[56] References Cited

U.S. PATENT DOCUMENTS

| | | | |
|---|---|---|---|
| 1,011,161 | 8/1911 | Packard | 602/30 |
| 1,055,810 | 3/1913 | Scholl | 602/30 |
| 1,240,286 | 9/1917 | Wood | 602/30 |
| 1,291,236 | 1/1919 | Stuck | 602/30 |
| 2,190,016 | 2/1940 | Day et al. | 602/30 |
| 2,332,473 | 10/1943 | Salander | 602/30 |
| 2,492,312 | 12/1949 | Mutler | 602/30 |
| 2,854,974 | 10/1958 | Ashton et al. | 128/894 |
| 3,088,461 | 5/1963 | Levitt | 128/894 |
| 3,178,724 | 4/1965 | Perschke | 473/205 X |
| 4,729,369 | 3/1988 | Cook | 602/30 |
| 4,940,046 | 7/1990 | Jacoby | 602/30 |

FOREIGN PATENT DOCUMENTS

| | | | |
|---|---|---|---|
| 514202 | 6/1955 | Canada | 602/30 |

*Primary Examiner*—Richard J. Apley
*Assistant Examiner*—Kim M. Lee
*Attorney, Agent, or Firm*—Hoffmann & Baron, LLP

[57] ABSTRACT

A bunion treatment apparatus for minimizing forces applied to a bunion on a foot surface of a patient includes a generally planar main portion and at least a first generally planar build-up portion. Both portions are constructed of flexible padding material and have predetermined thicknesses. The build-up portion has a smaller planform area than the main portion. The main portion is provided with a bunion-receiving aperture, which preferably extends therethrough, and the build-up portion is sized and shaped to fit around the bunion-receiving aperture. By providing one or more build-up portions with the main portion, the podiatric patient can custom-adjust the thickness and configuration of the bunion treatment apparatus to fit his own individual bunion. The main portion is also provided with a toe loop, which is formed with strain relief cutouts where its generally opposed edges intersect, to eliminate tearing of the main portion when the toe loop is placed over the toe of a patient.

12 Claims, 4 Drawing Sheets

BUNION TREATMENT APPARATUS AND METHOD

BACKGROUND OF THE INVENTION

1. Field of the Invention

The present invention relates to podiatric devices, and more particularly relates to a bunion treatment apparatus and method.

2. Description of the Prior Art

Bunion treatment apparatus are well known podiatric devices. Many individuals are afflicted with bunions of the foot. These may vary from individual to individual; some are minor, and some are major deformities which cause secondary problems affecting the entire physiology of the foot.

Prior art bunion treatment apparatus generally consist of a single planar sheet of padding material with a cut-out to surround the bunion. By using a bunion treatment apparatus with thickness greater than the bunion, the bunion treatment apparatus will absorb external forces to the surface of the foot that would otherwise put pressure on the bunion and cause discomfort to the patient. Bunion treatment apparatus may also include a so-called toe loop at one end of the device, which fastens about the patient's big toe to secure the apparatus in place on the medial aspect of the foot.

Although such bunion treatment apparatus are well known, and can give relief from painful bunions in some cases, they suffer from a number of deficiencies. For example, since bunions vary widely in size, shape and thickness from individual to individual, the prior art, single-sheet type of bunion treatment apparatus may be excessively thick for some persons, or too thin for others. In the latter case, the bunion will still be pressured by external forces (such as from a shoe), causing discomfort; in the former case, the excessively thick pad will feel clumsy to the patient. Further, the previously-mentioned toe loops are frequently formed with two or more intersecting sidewalls defining opposed edges. Fairly sharp corners are often present at the intersection of the sidewalls. These sharp corners result in stress concentrations when the bunion treatment apparatus is flexed to put the toe loop in place around the toe of the patient. Accordingly, the sharp corners are frequently sites where tearing of the bunion treatment apparatus begins.

In view of the deficiencies of prior art bunion treatment apparatus, there is a need for a bunion treatment apparatus which permits the individual patient to customize the configuration of the apparatus to match his or her own bunion. Furthermore, there is also a need for a bunion treatment apparatus which is not subject to tearing at the corners of the toe loop.

OBJECTS AND SUMMARY OF THE INVENTION

It is an object of the present invention to provide a bunion treatment apparatus which may be individually customized by a podiatric patient.

It is another object of the present invention to provide a bunion treatment apparatus with individually varying thickness.

It is yet another object of the present invention to provide a bunion treatment apparatus with a toe loop that is not subject to tearing due to the flexure induced when it is placed about the big toe of the patient.

It is a further object of the present invention to provide a bunion treatment apparatus which is configured for easy use by the patient.

In accordance with one form of the present invention, a bunion treatment apparatus for minimizing forces (such as from a shoe) applied to a bunion on a foot surface of a patient includes a generally planar main portion constructed of flexible padding material. The main portion has a predetermined main portion thickness, a main portion-planform area with an outer perimeter, and opposed first and second side surfaces. The main portion is formed with a bunion-receiving aperture which preferably extends therethrough. The bunion treatment apparatus also includes at least one generally planar build-up portion constructed of flexible padding material with a predetermined build-up portion thickness. The build-up portion also has a planform area which is less than the planform area of the main portion, and the build-up portion also has opposed first and second side surfaces. The build-up portion is sized and shaped to at least partially surround the bunion-receiving aperture.

The first side surface of the main portion is located against the foot surface of the patient with the bunion-receiving aperture surrounding the bunion and the opposed second side surface of the main portion facing away from the foot surface. The first side surface of the build-up portion is positioned adjacent the second side surface of the main portion with the build-up portion at least partially surrounding the bunion-receiving aperture, and the opposed second side surface of the build-up portion facing away from the foot surface.

Accordingly, the bunion treatment apparatus absorbs some or all of the forces which would otherwise be applied to the bunion. This results in greater individual comfort than is possible with prior art single-sheet devices.

In a method of relieving pain associated with a bunion on a foot surface of a patient by minimizing forces applied to the bunion, in accordance with the present invention, a generally planar main portion of a bunion treatment apparatus is applied to the foot surface of the patient. The main portion is constructed of flexible padding material and has a predetermined main portion thickness. The main portion also has a planform area with an outer perimeter, and opposed first and second side surfaces. The main portion also has a bunion receiving aperture, which preferably extends therethrough. The first side of the main portion is located against the foot surface of the patient with the bunion receiving area surrounding the bunion and the opposed second side surface of the main portion facing away from the foot surface.

The method also includes applying to the opposed second side surface of the generally planar main portion of the bunion treatment apparatus at least a first generally planar build-up portion constructed of flexible padding material and having a predetermined build-up portion thickness. The build-up portion also has a planform area, and first and second opposed side surfaces. The build-up portion planform area is less than the main portion planform area and the build-up portion is sized and shaped to at least partially surround the bunion receiving area. The first side surface of the build-up portion is positioned adjacent the second side surface of the main portion with the build-up portion at least partially surrounding the bunion receiving area, and the opposed second side surface of the build-up portion facing away from the foot surface of the patient.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
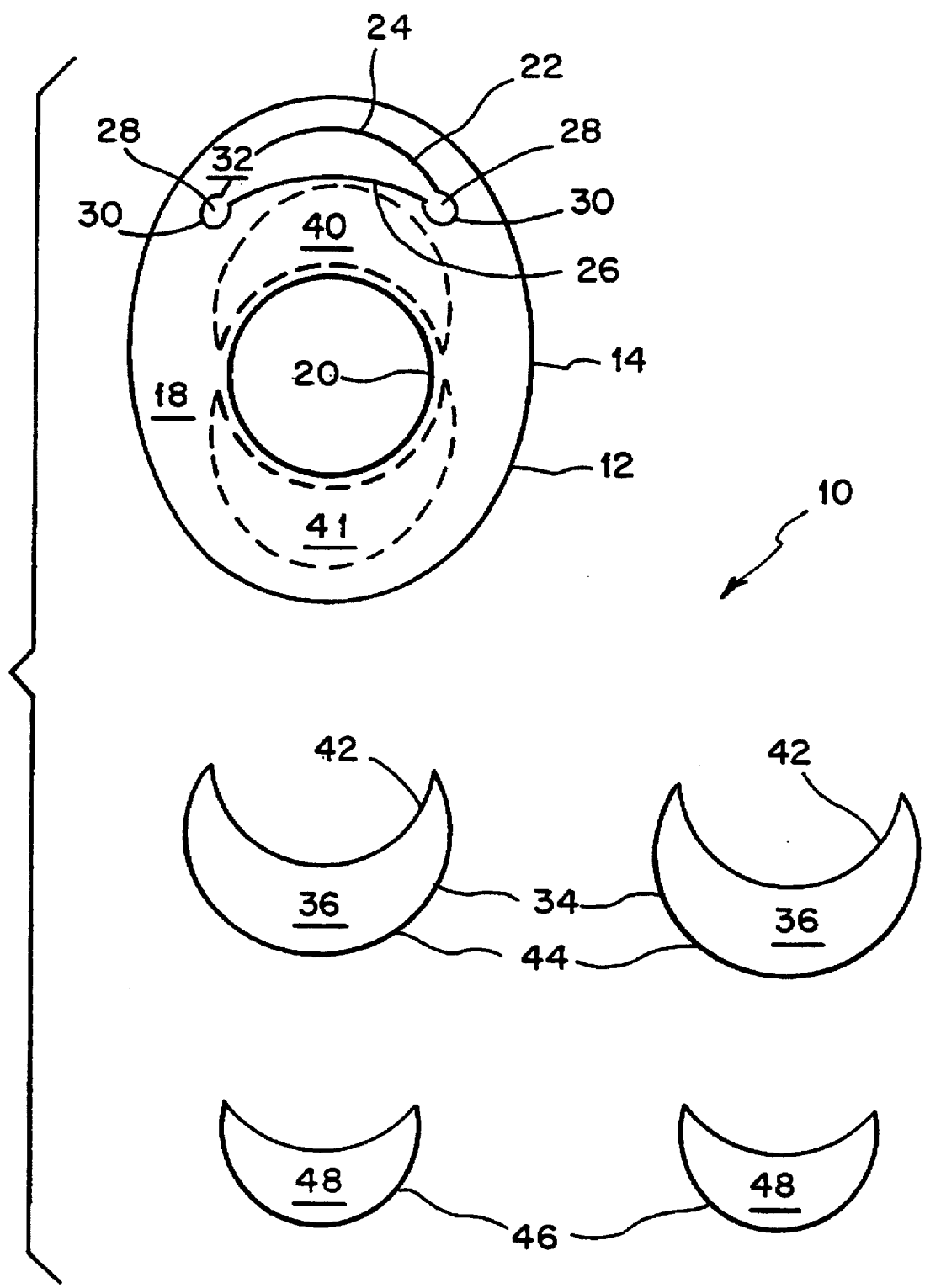
FIG. 1 is a plan view of a bunion treatment apparatus in accordance with the present invention, including a main portion and two each of first and second build-up portions.

Referring to FIG. 1, a bunion treatment apparatus, designated generally as 10, includes a generally planar main portion 12 constructed of flexible padding material. The main portion has a predetermined main portion thickness. Preferably, this thickness is approximately 5/32 inch, and the main portion is preferably formed from a laminated two-part foam including a 3/32 inch layer of slow recovery foam and a 1/16 inch layer of fast recovery foam. Preferably, the thickness of the main portion is uniform, but it may be varied for purposes to be discussed below. The main portion has a planform area defined by a sidewall at outer perimeter 14, which is preferably oblong in shape. The main portion also includes opposed first and second side surfaces (i.e., top and bottom sides) designated respectively as 16 and 18. It will be appreciated that surface 16 is not visible in FIG. 1.

Main portion 12 is formed with a bunion-receiving aperture 20, which is preferably formed through the thickness of the main portion, although it may also extend only partially through main portion 12. Preferably, main portion 12 is formed with a toe loop 22 having first and second generally opposed edges 24 and 26. The edges are preferably curved and intersect at end intersection points 28. Preferably, strain relief cutouts 30 (preferably circular) are provided at the end intersection points to minimize any tendency of the toe loop to tear. The first edge 24 of toe loop 22 is preferably located adjacent to outer perimeter 14 of main portion 12, thereby defining a toe loop strip 32 between first edge 22 and outer perimeter 14.

Still referring to FIG. 1, bunion treatment apparatus 10 preferably also includes at least a first generally planar build-up portion 34 constructed of flexible padding material and having a predetermined build-up portion thickness. Two first portions 34 are shown in the figure. The predetermined thickness of the first build-up portion is preferably 1/16 inch and the build-up portion is preferably constructed of the same fast recovery foam as the 1/16 inch layer of the main portion. The predetermined thickness of first build-up portion 34 is preferably uniform. Build-up portion 34 has a planform area which is less than the planform area of main portion 12. First build-up portion 34 includes opposed first and second side surfaces 36 and 38 respectively. It will be appreciated that second side surface 38 of first build-up portion 34 is not visible in FIG. 1.

First build-up portion 34 is sized and shaped to at least partially surround bunion-receiving aperture 20 of main portion 12. Preferably, second edge 26 of toe loop 22 on main portion 12 has a predetermined curved shape defining a build-up portion receiving area 40 on opposed second side 18 of main portion 12, between the second edge 26 of toe loop 22 and the bunion receiving aperture 20. Further, another build-up portion receiving area 41 is preferably defined between aperture 20 and perimeter 14 of main portion 12, substantially opposite area 40.

Preferably, bunion-receiving aperture 20 is generally circular and first build-up portion 34 is generally crescent-moon-shaped having an inner arcuate edge 42 with substantially the same radius as that of the bunion-receiving aperture 20. First build-up portion 34 also preferably has an outer edge 44 curved to fit within either of build-up portion receiving areas 40 and 41.

Preferably, bunion treatment apparatus 10 also includes at least a second generally planar build-up portion 46, also constructed of flexible padding material. Two second portions 46 are shown in the figure. Second build-up portion 46 has a predetermined second build-up portion thickness, which is preferably 1/16 inch so that the total thickness of main portion 12, first build-up portion 34 and second build-up portion 46 is 9/32 inch. Preferably, the thickness is uniform and the second build-up portion is constructed from the same material as the first build-up portion. Second build-up portion 46 also has a planform area which is less than the planform area of the first build-up portion, and has opposed first and second side surfaces 48 and 50 respectively. It will be appreciated that second side surface 50 of second build-up portion 46 is not visible in FIG. 1. Second build-up portion 46 is sized and shaped to at least partially surround bunion-receiving aperture 20. Preferably, second build-up portion 46 is also generally crescent-moon-shaped.

Figure 2:
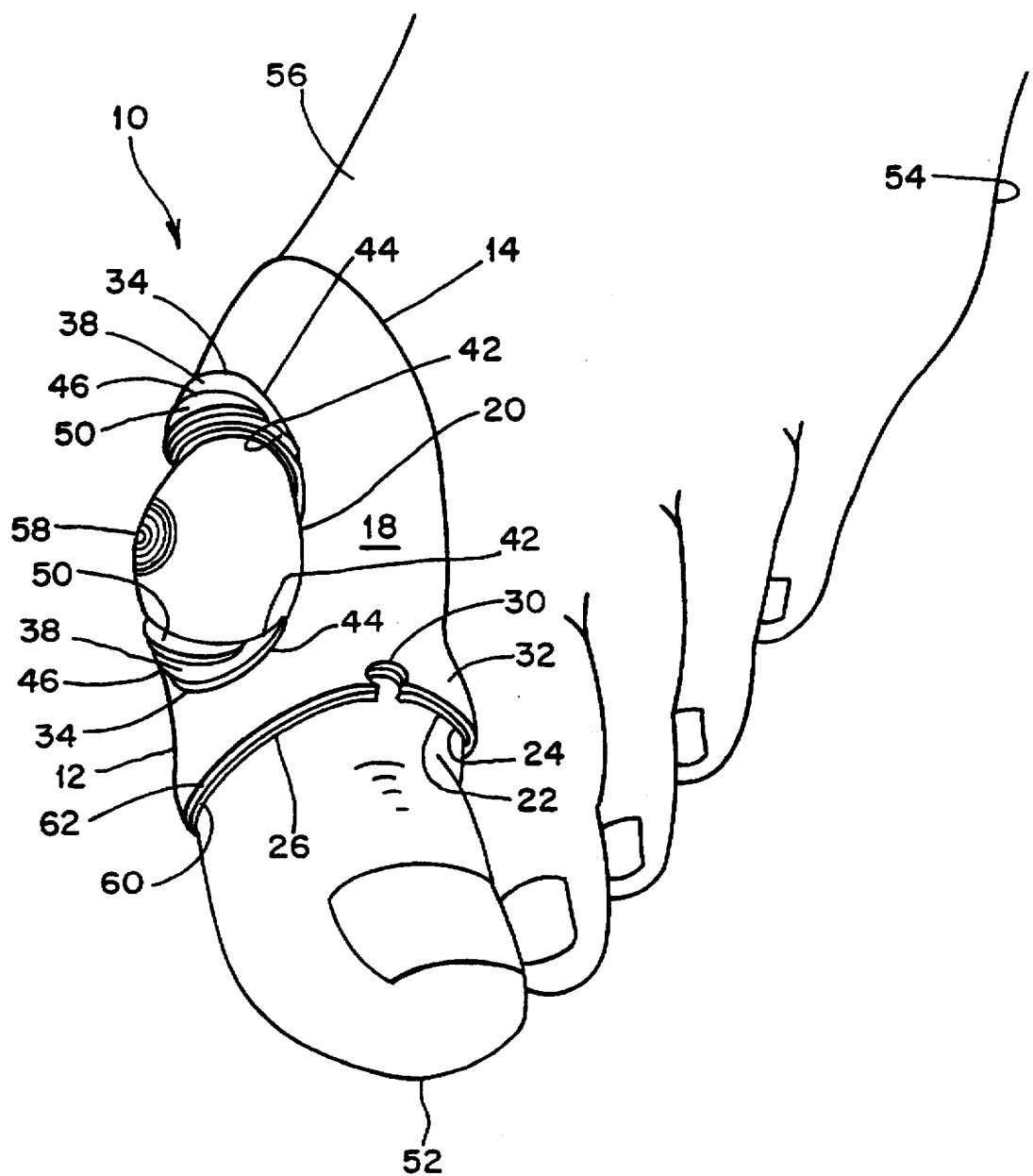
FIG. 2 is a perspective view of a bunion treatment apparatus according to the present invention applied to the medial aspect of the foot and secured about the left big toe of a patient.

Referring now to FIG. 2, bunion treatment apparatus 10 is shown as secured to the left big toe 52 of human foot 54. First side 16 (not visible) of main portion 12 is located against foot surface 56 (the medial aspect) of foot 54. Toe 52 is placed through toe loop 22 with toe loop strip 32 over toe 52 to secure main portion 12 in place. Strain relief cutouts 30 prevent any tearing of main portion 12 due to flexure of toe loop strip 32 with respect to the remainder of main portion 12. Two first build-up portions 34 are applied to main portion 12, one each in build-up portion receiving area 40 and 41. Two second build-up portions 46 are also applied, one to each first buildup portion 34. Bunion 58 is surrounded by bunion-receiving aperture 20 and the first and second build-up portions; accordingly, it is protected from external forces (such as those from a shoe). It will be appreciated that main portion 12 and first and second build-up portions 34 and 46 respectively can flex so as to conform to the local curvature of the medial aspect of the foot in the region of the bunion.

Referring now to FIGS. 3 and 4, it can again be seen that main portion 12 is applied to surface 56 of foot 54 with first side 16 (not visible in FIG. 3) adjacent surface 56. Bunion 58 is received in bunion receiving aperture 20. Opposed second side 18 of main portion 12 faces away from foot surface 56. The first side surface 36 (not visible in FIG. 3) of each first build-up portion 34 is positioned adjacent second side surface 18 of main portion 12. First build-up portions 34 at least partially surround aperture 20. Opposed second side surfaces 38 of first build-up portions 34 face away from foot surface 56.

Figure 3:
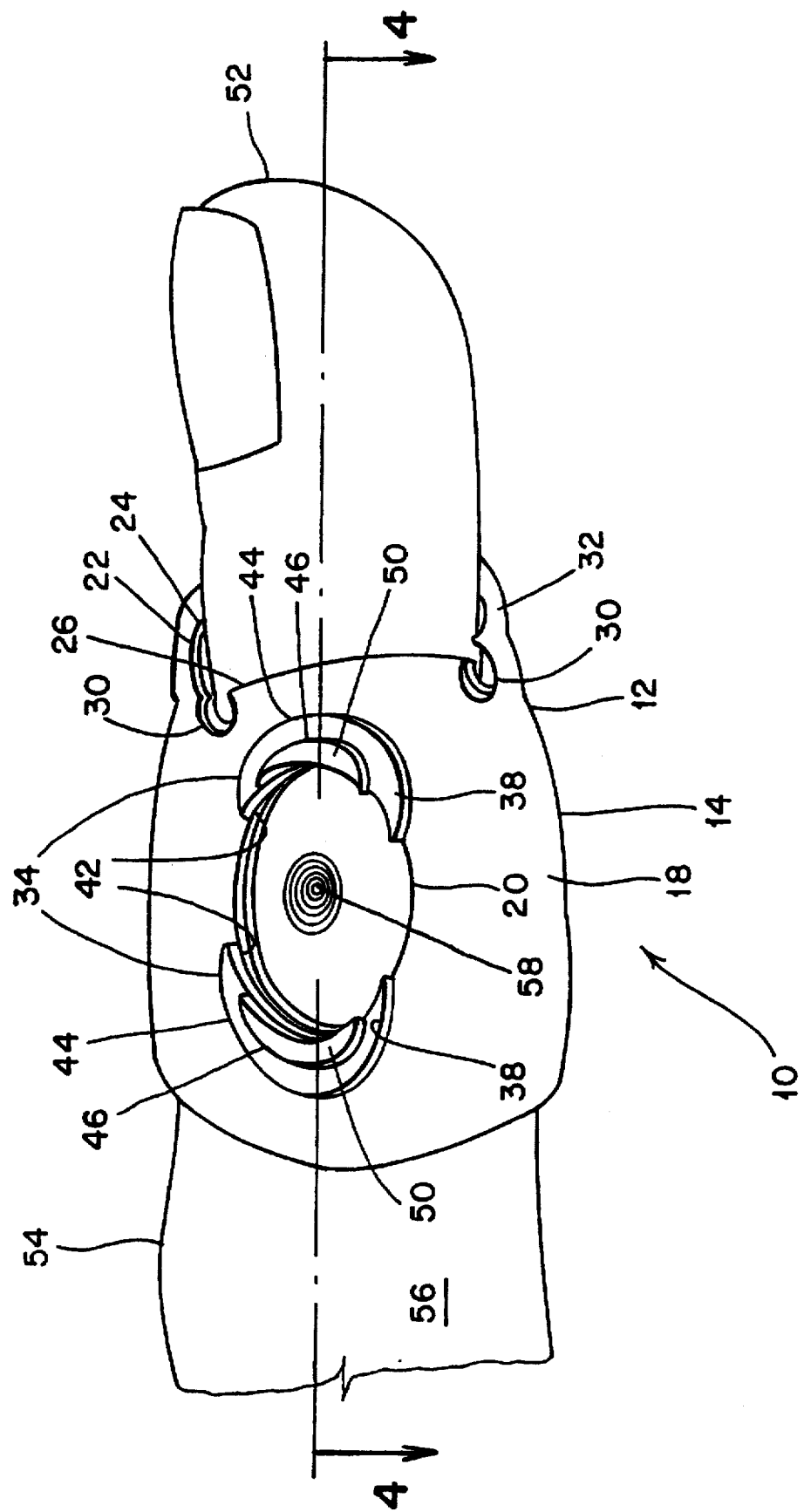
FIG. 3 is a side elevation view of a bunion treatment apparatus in accordance with the present invention secured in place about the left big toe of a patient for relieving discomfort from a bunion located on the medial aspect of the patient's foot.
Figure 4:
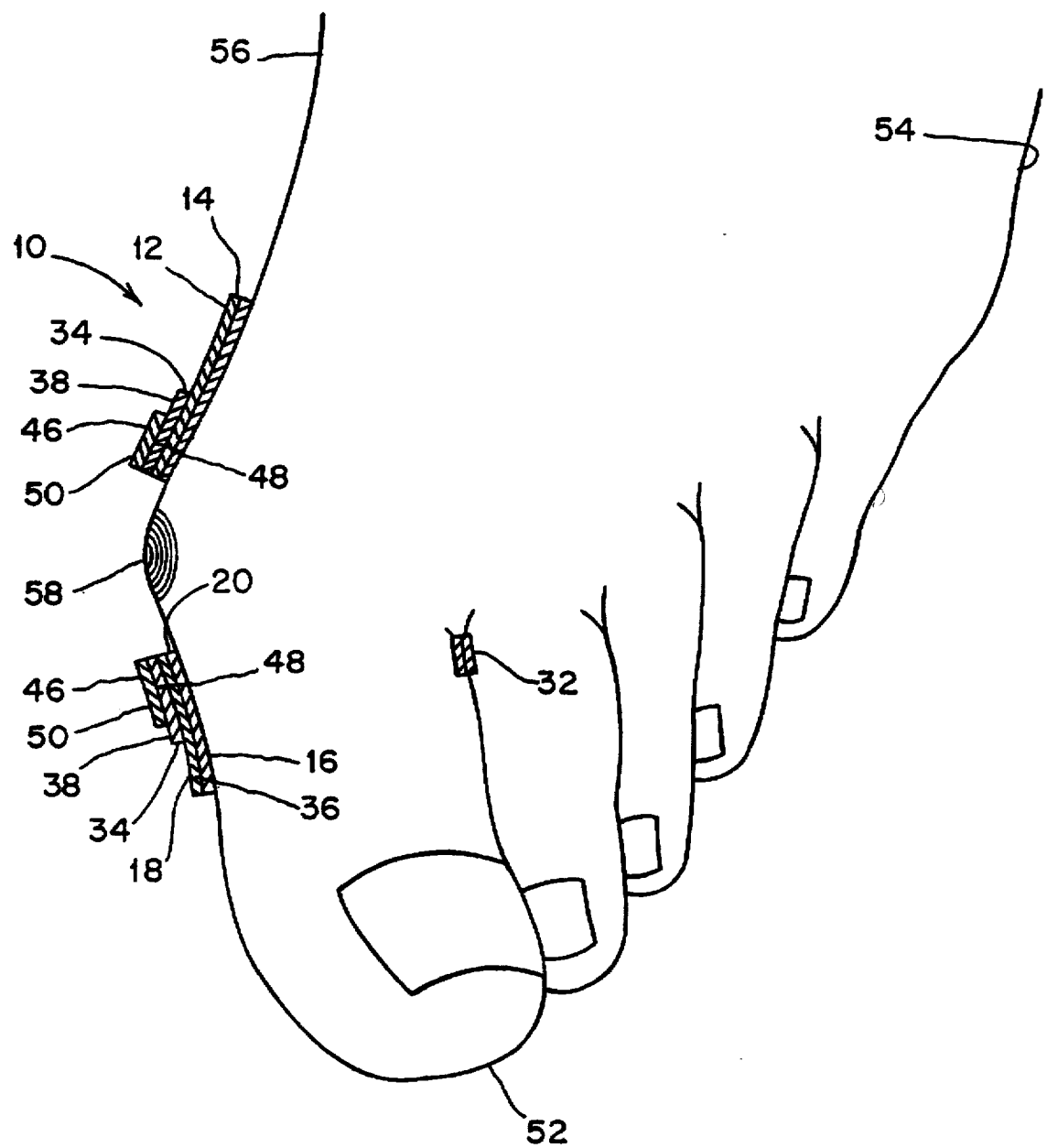
FIG. 4 is a sectional view taken along line 4—4 of FIG. 2.

The bunion treatment apparatus 10 depicted in FIGS. 3 and 4 includes two first build-up portions 34 and two second build-up portions 50. It will be appreciated that first side surfaces 36 and 48 of first build-up portions 34 and second build-up portions 46 respectively may be provided with a layer of hypo-allergenic, biocompatible adhesive, with pull-off backing, for purposes of securing them in place. Second build-up portions 46 are located against second side surfaces 38 of first build-up portions 34 with the second build-up portions at least partially surrounding the bunion receiving aperture 20, and with the opposed second sides 50 of second build-up portions 46 facing away from the foot surface 56.

Although FIGS. 3 and 4 depict first build-up portions 34 applied onto the build-up portion receiving areas 40 and 41 of main portion 12, and second build-up portions 46 applied respectively to the first build-up portions 34, it is to be understood that many different configurations are possible. For example, a first build-up portion could be applied on one side of bunion-receiving aperture 20 and a second build-up portion on the other side. Other combinations and permutations for the arrangement of build-up portions 34 and 46 will be apparent to those skilled in the art. Further, it is to be understood that the build-up portions 34 and 46 may have other than a crescent-moon shape. For example, they may be formed as annular rings of material to completely surround bunion-receiving aperture 12. Further, bunion-receiving aperture 20 need not be circular; any other convenient shape is also possible.

When providing a bunion treatment apparatus, it is desirable to prevent painful forces from being transmitted to the bunion, and yet to interfere as little as possible with normal motion of the foot. Accordingly, it is generally desirable to locate the maximum thickness of the apparatus adjacent the bunion, to absorb potential pain-inducing forces, with a lower thickness in outlying regions to minimize interference with normal foot motion. It will be appreciated that in the configuration shown in FIGS. 3 and 4, the thickness of the assembled bunion treatment apparatus increases from the outer perimeter 14 of main portion 12 towards the bunion-receiving aperture 20, by virtue of the build-up portions 34 and 46.

Uniform thickness is preferred for main portion 12 and first and second build-up portions 34 and 46, for ease of manufacturing. However, it is to be understood that the main portion 12 and/or first and second build-up portions 34 and 46 may be provided with a varying thickness which gradually decreases away from the bunion receiving aperture, to result in a more smooth variation of the thickness and even greater comfort for the patient than where all components have uniform thickness.

In its preferred form, bunion treatment apparatus 10 is configured for easy use by the patient and is packaged as part of a kit including main portion 12 with two substantially similar first build-up portions 34 and two substantially similar second build-up portions 46. In order to assist the patient with correct assembly of the device, build-up portion receiving areas 40 and 41 may be provided with assembly-aiding visual cues such as the dashed lines shown in FIG. 1 which outline the shape of the first build-up portion 34, for example. Further, as best seen in FIG. 2, main portion 12 of bunion treatment apparatus 10 may include color coded bottom and top layers 60 and 62 respectively. Bottom layer 60 (preferably a 3/32 inch layer of slow recovery foam), or surface 16, can have a color (for example, white) which is different from top layer 62 (preferably a 1/16 inch layer of fast recovery foam) or surface 18 (for example, blue), in order to visually indicate to the patient which side of the apparatus is intended to face the foot and which side to face away from the foot. The build-up portions can have the same color as top layer 62 (or surface 18), in order to indicate to the patient that the build-up portions are to be worn facing away from the foot and situated on surface 18.

If desired, the kit can include additional components for even greater versatility. For example, at least a third build-up portion can be provided which is identical to the first build-up portion except for being formed with a different thickness. Similarly, at least a fourth build-up portion can be provided which is identical to the second build-up portion except for being formed with a different thickness. In this way, the bunion treatment apparatus can be more closely matched with a variety of bunion sizes and shapes.

Although it is envisioned that a kit will be the most common form in which the present invention is offered for sale, it is to be understood that it would also be possible to sell a main portion and build-up portions separately, or even to sell a main portion as a stand-alone product. In the latter case, one would lose the "custom-fit" capability, but would still obtain the benefits of the toe loop with strain relief cutouts.

In a method according to the present invention, a main portion 12 of a bunion treatment apparatus 10 in accordance with the invention is applied to the foot surface 56 of a patient with the bunion-receiving aperture 20 surrounding the bunion 58. One or more build-up portions 34, 46 in accordance with the present invention are attached to the main portion 12 as described above. This attachment may take place either before the main portion is applied to the foot 54, or afterwards. Once installed, the assembled bunion treatment apparatus 10 relieves pain associated with the bunion 58 on the foot surface 56 of the patient by minimizing forces applied to the bunion, such as from a shoe. As used herein, minimizing includes at least a significant reduction, and preferably includes a substantial reduction or complete elimination of any forces applied to the bunion. The bunion treatment apparatus acts as a cushion to absorb forces that would otherwise be transmitted to the bunion. If the bunion treatment apparatus extends away from the surface of the foot beyond the bunion, it will absorb all such forces until it has compressed to a level equal with the height of the bunion, at which time some force will be applied to the bunion. Even if some force is still applied to the bunion, it will be much less than without the bunion treatment apparatus and therefore less likely to cause discomfort for the patient. It will be appreciated that to minimize or prevent any force from being transmitted through the bunion, it is necessary to properly select both the thickness and the material of the bunion treatment apparatus main and build-up portions.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A bunion treatment apparatus for minimizing forces applied to a bunion on a foot surface of a patient, said bunion treatment apparatus comprising:

a generally planar main portion constructed of flexible padding material and having a predetermined main portion thickness, a main portion planform area with an outer perimeter, and opposed first and second side surfaces, said second side surface being an exterior surface, said main portion having a bunion-receiving aperture formed at least partially therethrough; and at least a first generally planar build-up portion separate from said planar main portion and being constructed of flexible padding material and having a predetermined build-up portion thickness, a build-up portion planform area, and opposed first and second side surfaces, said build-up portion planform area being less than said main portion planform area, said build-up portion being sized and shaped to at least partially surround said bunion-receiving aperture, said first side of said main portion adapted to be located against the foot surface of the patient, said bunion-receiving aperture adapted to surround the bunion and said opposed exterior second side surface of said main portion facing away from the foot surface, said first side of said build-up portion being positioned adjacent said opposed exterior second side surface of said main portion with said build-up portion at least partially surrounding said bunion-receiving aperture and said opposed exterior second side surface of said build-up portion facing away from the foot surface, whereby said bunion treatment apparatus minimizes the forces applied to the bunion.

2. A bunion treatment apparatus in accordance with claim 1, wherein said predetermined main portion thickness is greater than said predetermined build-up portion thickness.

3. A bunion treatment apparatus in accordance with claim 2, wherein said predetermined main portion thickness is substantially uniform and is approximately 1/8 inch, and wherein said predetermined build-up portion thickness is substantially uniform and is approximately 1/16 inch.

4. A bunion treatment apparatus in accordance with claim 1, wherein said main portion is formed with a toe loop having first and second generally opposed edges with end intersection points, said first edge being located adjacent said outer perimeter of said main portion, thereby defining a toe loop strip between said first edge of said toe loop and said outer perimeter.

5. A bunion treatment apparatus in accordance with claim 4, wherein said main portion is formed with strain relief cutouts at said end intersection points of said edges of said toe loop.

6. A bunion treatment apparatus in accordance with claim 4, wherein:

said second edge of said toe loop has a predetermined shape defining a build-up portion receiving area on said opposed second side of said main portion between said bunion-receiving aperture and said second edge of said toe loop; and said build-up portion is sized and shaped to fit into said build-up portion receiving area.

7. A bunion treatment apparatus in accordance with claim 6, wherein:

said outer perimeter of said main portion is generally oblong;

said bunion-receiving aperture is generally circular;

said second edge of said toe loop is curved; and said build-up portion is generally crescent-moon-shaped, having an inner arcuate edge with substantially the same radius as said bunion-receiving aperture and an outer edge curved to fit within said build-up portion receiving area.

8. A bunion treatment apparatus in accordance with claim 1, further comprising a layer of adhesive with pull-off backing applied to said first side of said build-up portion.

9. A bunion treatment apparatus in accordance with claim 1, further comprising at least a second generally planar build-up portion constructed of flexible padding material and having a predetermined second build-up portion thickness, a second build-up portion planform area less than said planform area of said first build-up portion, and opposed first and second side surfaces, said second build-up portion being sized and shaped to at least partially surround said bunion-receiving aperture, said first side surface of said second build-up portion being located against said second side surface of said first build-up portion with said second build-up portion at least partially surrounding said bunion-receiving aperture and said opposed second side surface of said second build-up portion facing away from the foot surface.

10. A method of relieving pain associated with a bunion on a foot surface of a patient by minimizing forces applied to the bunion, said method comprising the steps of:

(a) applying to the foot surface of the patient a generally planar main portion of a bunion treatment apparatus, said generally planar main portion being constructed of flexible padding material and having a predetermined main portion thickness, a main portion planform area with an outer perimeter, and opposed first and second sides, said second side being an exterior side, said main portion having a bunion-receiving aperture formed at least partially therethrough, said first side of said main portion being located against the foot surface of the patient with said bunion receiving aperture surrounding the bunion and said opposed second side of said main portion facing away from the foot surface; and (b) applying to said opposed exterior second side of said generally planar main portion of said bunion treatment apparatus at least a first generally planar build-up portion constructed of flexible padding material and having a predetermined build-up portion thickness, a build-up portion planform area, and first and second sides, said build-up portion planform area being less than said main portion planform area, said build-up portion being sized and shaped to at least partially surround said bunion-receiving aperture, said first side of said build-up portion being positioned adjacent said opposed exterior second side of said main portion with said build-up portion at least partially surrounding said bunion receiving aperture and said opposed second side of said build-up portion facing away from the foot surface.

11. A bunion treatment apparatus kit comprising:

a generally planar main portion constructed of flexible padding material and having a predetermined main portion thickness, a main portion planform area with an outer perimeter, and opposed first and second side surfaces, said second side surface being an exterior surface, said main portion having a bunion-receiving aperture at least partially therethrough, said main portion having a build-up portion receiving area defined on said second side surface and highlighted by visual cues;

at least a first generally planar build-up portion separate from said planar main portion and being constructed of flexible padding material and having a predetermined first build-up portion thickness, a first build-up portion planform area, and opposed first and second side surfaces, said first build-up portion planform area being less than said main portion planform area, said first build-up portion being sized and shaped to at least partially surround said bunion-receiving aperture, said first side surface of said first build-up portion including an adhesive layer; and at least a second generally planar build-up portion separate from said planar main portion and being constructed of flexible padding material and having a predetermined second build-up portion thickness, a second build-up portion planform area less than said planform area of said first build-up portion, and opposed first and second side surfaces, said second build-up portion being sized and shaped to at least partially surround said bunion-receiving aperture, said first side surface of said second build-up portion including an adhesive layer.

12. A bunion treatment apparatus kit in accordance with claim 11, further comprising:

at least a third build-up portion constructed of flexible padding material and having a predetermined third build-up portion thickness which is different from said first build-up portion thickness, a third build-up portion planform area which is equal to said first build-up portion planform area, and opposed first and second side surfaces, said third build-up portion being sized and shaped to at least partially surround said bunion-receiving aperture, said first side surface of said third build-up portion including an adhesive layer; and at least a fourth build-up portion constructed of flexible padding material and having a predetermined fourth build-up portion thickness which is different from said second build-up portion thickness, a fourth build-up portion planform area which is equal to said second build-up portion planform area, and opposed first and second side surfaces, said fourth build-up portion being sized and shaped to at least partially surround said bunion-receiving aperture, said first side surface of said fourth build-up portion including an adhesive layer.

* * * * *